United States Patent [19]

Kapil et al.

[11] Patent Number: 5,254,568

[45] Date of Patent: Oct. 19, 1993

[54] BENZOPYRANS AS ANTIESTROGENIC AGENTS

[75] Inventors: Randhir S. Kapil, Jammu-Tawi; Susheel Durani, Bombay; Janak D. Dhar; Bachu S. Setty, both of Lucknow, all of India

[73] Assignee: Council of Scientific & Industrial Research, New Delhi, India

[21] Appl. No.: 965,608

[22] Filed: Oct. 22, 1992

Related U.S. Application Data

[63] Continuation of Ser. No. 582,249, Sep. 13, 1990, abandoned.

[51] Int. Cl.$^5$ .................. A61K 31/445; A61K 31/40; C07D 405/12
[52] U.S. Cl. ..................................... 514/320; 514/422; 546/196; 548/525
[58] Field of Search ................. 546/196; 548/525; 514/320, 422

[56] References Cited

U.S. PATENT DOCUMENTS 3,340,276  9/1967  Carney et al. ..................... 546/195
3,471,520 10/1969 Irmscher et al. .................... 544/357

Primary Examiner—C. Warren Ivy
Assistant Examiner—Celia Chang
Attorney, Agent, or Firm—Ladas & Parry

[57] ABSTRACT

The present invention provides compounds of formula

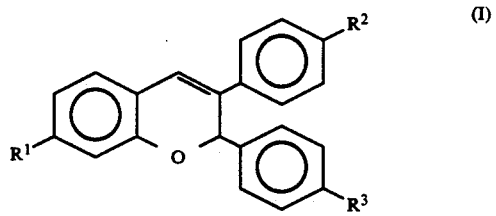

wherein $R^1$ and $R^2$, which may be the same or different, are each —H, —OH, alkoxy of 1 to 17 carbon atoms or alkoxycarbonyl of 2 to 18 carbon atoms and $R^3$ is

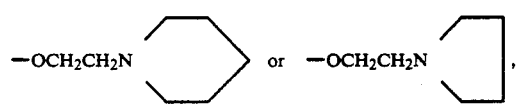

are useful in the treatment of an estrogen dependent condition such as breast cancer.

12 Claims, No Drawings

BENZOPYRANS AS ANTIESTROGENIC AGENTS

This is a continuation of copending application Ser. No. 07/582,249 filed on Sep. 13, 1990, now abandoned.

The present invention relates to novel benzopyrans which are anti-estrogenics and possess significant activity against implantation and breast cancer. The invention also relates to a process for the synthesis of these benzopyrans.

A number of anti-estrogens have been synthesised in recent years. These non-steroidal compounds have been developed on the basis of their structure activity relationship established by Dodds and his co-workers and have been found to be more potent than compounds known hereto (Dodds, E. C., *J.Pharm. Pharmacol.*, 1, 137 (1949), Dodds, E. C., Folley, S. J., Glascuck, R. F. and Lawson, W., *Biochem.J.*, 68, 161 (1958); Dodds, E. C., Goldberg, L., Lawson, W. and Robinson, R., *Part I Proc. Royal Soc. B.*, 127, 140 (1939).

These anti-estrogens consist essentially of diarylethylenes (DAE) and triarylethylenes (TAE) and examples of the more important of such compounds in terms of potency include tamoxifen, 4-hydroxytamoxifen, centchroman and hydroxycentchroman.

Tamoxifen and 4-hydroxytamoxifen can be represented by the formula:

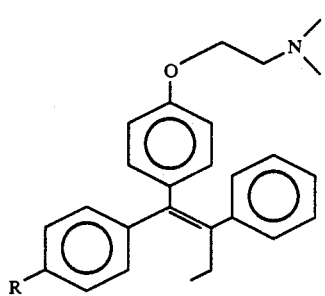

wherein when R is hydrogen the compound is tamoxifen and when R is OH the compound is 4-hydroxytamoxifen.

Centchroman and hydroxycentchroman can be represented by the formula:

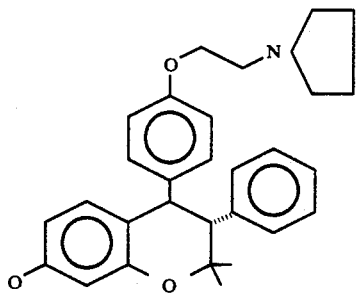

wherein when R is Me the compound is centchroman and when R is H the compound is hydroxcentchroman.

Unfortunately, almost all hitherto known anti-estrogens, including DAE's and TAE's evince varying degrees of agonistic activity. This is a drawback in their use as drugs since it is the estrogen antagonistic activity of DAE's and TAE's which makes them important.

It has therefore long been desired to develop novel estrogen antagonists which have extremely low, preferably essentially no agonistic activity, viz. which do not evince estrogenecity.

A study of known DAE's and TAE's has established that it is the presence of glyceryl ether or w-alkylaminoalkoxy chain in the para position in one of the geminal aryl groups that is essential for estrogen antagonistic activity. Two or three methylene groups and the nitrogen atom substituted with one or two short alkyl or single cycloalkyl residue (piperidino or pyrrolidino) in the said chain is the optimum requirement for estrogen antagonistic activity of the prototypes. Among TAEs, molecular geometry plays an important role in determining an agonist/antagonist balance. In most compounds, estrogen antagonist activity is restricted to only those isomers having two of the vicinal aryl groups, without the basic ether chain, in trans geometry to each other. The corresponding cis isomers are estrogens devoid of antagonistic activity.

The present invention therefore provides a compound of the formula I

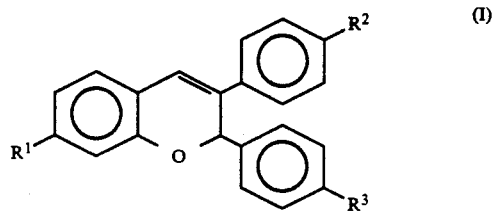

wherein $R^1$ and $R^2$, which may be the same or different, are each —H, —OH, alkoxy of 1 to 17 carbon atoms or alkoxycarbonyl of 2 to 18 carbon atoms, and $R^3$ is

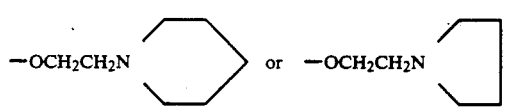

There are several preferred embodiments. In one preferred embodiment $R^1$ and $R^2$ are each independently H, OH or $C_{1-4}$ alkoxy.

Other preferred embodiments include (i) $R^1$ being H or (ii) $R^1$ and $R^2$ each being an acyl or alkoxy group.

$R^3$ is preferably a 2-piperidinoethoxy group. Specific compounds within formula I include 2-[4-[2-(1-piperidino)ethoxy]phenyl]-3-[4-hydroxyphenyl]-2H-1-benzopyran, 2-[4-[2-(1-piperidino)ethoxy)phenyl]-3-phenyl-7-methoxy-2H-1-benzopyran, 2-[4-[2-(1-piperidino) ethoxy]phenyl]-3-[4-hydroxyphenyl]-7-hydroxy-2H-1-benzopyran.

The present invention also provides a process for the synthesis of these benzopyrans of the formula:

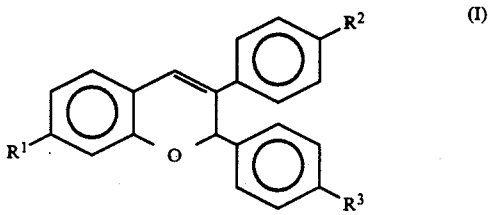

wherein $R^1$, $R^2$ and $R^3$ have the meanings stated above. This process comprises reacting a compound of formula II

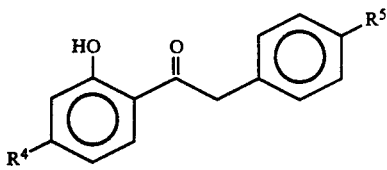

in which $R^4$ and $R^5$ are $R^1$ and $R^2$ respectively, or a protected hydroxy group, with 4-hydroxybenzaldehyde to produce a compound of the formula III

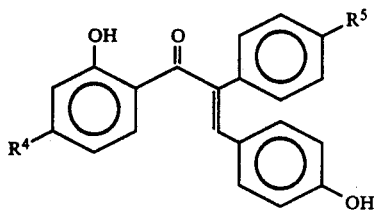

forming a compound of formula IV

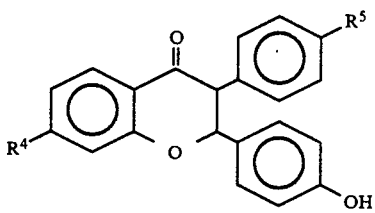

reacting this compound with a compound of formula V

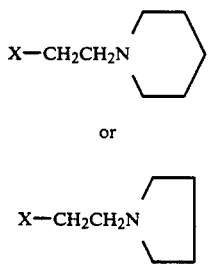

in which X is a halide to form a compound of formula VI

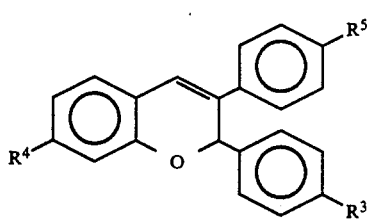

and, if necessary, deprotecting and acylating or alkylating $R^4$ and $R^5$.

In the preferred embodiment in which in the compound I produced, $R^1$ is H, preferably in the above process $R^4$ is H and $R^5$ is a protected hydroxy group.

When the process is used to produce a compound in which $R^1$ and $R^2$ are each alkoxy or carboxy then $R^4$ and $R^5$ may be $R^1$ and $R^2$ respectively or may each be in the form of a protected hydroxy group. If $R^1$ or $R^2$ is a hydroxy group then $R^4$ or $R^5$ respectively in the above process is preferably in the form of a protected hydroxy group. If $R^4$ or $R^5$ is a protected group then preferably the protecting group is 3,4-dihydropyran. The 3,4-dihydropyran may be reacted with a compound of formula IX

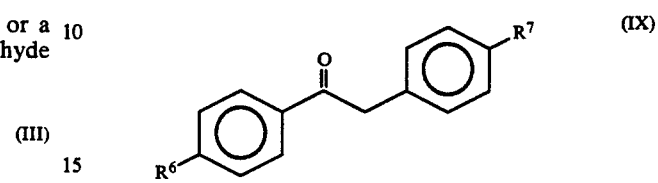

where one of $R^6$ and $R^7$ is a hydroxy group and the other is hydrogen or a hydroxy group or an alkoxy or carboxy group, to form a tetrahydropyranyl ether. Preferably the reaction is carried out in the presence of a sulphonic acid, such as para-toluene sulphonic acid or the like in an ether solvent, such as, dioxan or the like. The reaction may be effected for a period of up to 4 hours and the crude reaction product, after stipulated processing, may be purified e.g. by crystallization from a petroleum solvent such as hexane or by rapid chromatography over silica gel.

The reaction of the compound of formula II with the 4-hydroxybenzaldehyde may be effected in the presence of a cyclic or open chain secondary and/or tertiary amino base such as piperidine or triethyl amine, and an aromatic hydrocarbon solvent such as benzene or the like. The solvent may be added at periodic intervals to replenish its loss during the reaction. This reaction may be effected for a period of about 30 hours. Thereafter, the reaction mixture may be cooled and washed with water, the organic layer separated, dried under $Na_2SO_4$ and concentrated. The solidified material may be filtered off, washed with a halogenated solvent such as chloroform, methylene dichloride or the like to give a compound of the formula III. Generally the compound III will be produced as a mixture with a compound of formula VIII

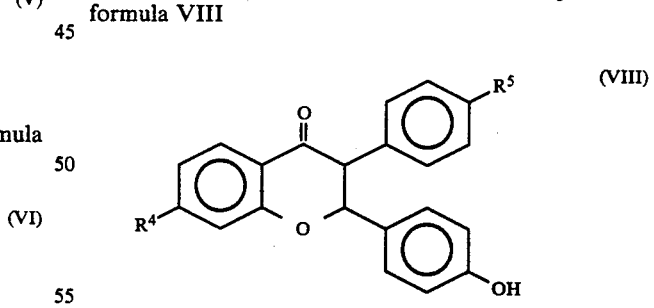

For example the product mixture may contain a ratio of compound VIII to compound III of 1.0:1.5. The filtrate containing compounds III and VIII may be concentrated, chromatographed and eluted with an eluate of increasing polarity such as ethyl acetate in hexane or the like, thereby separating out the compound of formula III.

The compound of the formula III may be converted to a compound of formula IV reduction, for example by treating with a hydride such as sodium borohydride or the like in an alcoholic solvent such as ethyl alcohol or the like. Cyclodehydration may also be carried out, typically work up of the product e.g. thermal work up may cause cyclodehydration. The hydride may be added in different proportions, at intervals of 10 to 15 minutes at room temperature under stirring. The reaction may be continued for a period of up to 12 to 15 hours. The reaction product after concentration, pH adjustment and extraction with a polar solvent such as ethyl acetate is purified by chromatography e.g. flash chromatography over silica gel to yield a compound of the formula IV. The compound of formula IV is treated with a piperidino- or pyrrolidinoalkyl halide, preferably in the presence of a basic catalyst such as potassium carbonate and a suitable ketonic solvent such as acetone or the like. This may be followed by purification by chromatography e.g. on alumina using hexane or a mixture thereof with a polar solvent to yield a compound of formula VI.

If $R^4$ and $R^5$ are not protected hydroxy groups then the compound produced is a compound of formula I. If $R^4$ or $R^5$ is a protected hydroxy group then the protecting group(s) may be removed by known methods e.g. by use of an acid such as hydrochloric acid in an alcoholic solvent such as ethanol. The deprotected hydroxy group(s) may, if desired, be alkylated or acylated by known methods to give other compounds of formula I.

The unprotected starting compound of formula (II)'

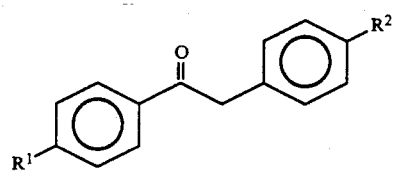

where $R^1$ and $R^2$ are as herein before defined can be prepared by methods known in the art. For example, when $R^1$ is H and $R^2$ is OH it can be prepared by condensation of phenol with 4-methoxy-phenylacetyl chloride (in turn prepared from 4-methoxy-phenylacetic acid) to afford an ester which on typical Fries rearrangement in the presence of anhydrous aluminium chloride yields a mixture which can be resolved chromatographically to afford the desired starting material. It can be characterised by its physical and spectral data.

When $R^1$ is e.g. methoxy and $R^2$ is as hereinbefore defined the starting compound II' may be prepared by Friedel-Crafts acylation of a corresponding phenol, such as 3-methoxyphenol or the like, with a suitable substituted or unsubstituted phenylacetyl chloride using a catalyst, such as anhydrous aluminium chloride. The resultant produce may be purified by steam distillation and/or column chromatography.

In turn, when $R^1$ and $R^2$ are both OH the starting compound can be prepared by Friedal-Crafts acylation of resorcinol with 4-methoxyphenyl acetyl chloride. This reaction affords a mixture of trihydroxydeoxybenzoin and methoxy dihydroxydeoxybenzoin. The latter compound may be converted into the desired trihydroxy compound by heating it with anhydrous pyridine hydrochloride.

The following examples illustrate the invention.

EXAMPLE-AI

Preparation of Monotetrahydropyranyl Ether of Dihydroxydeoxybenzoin
(1-[2-Hydroxyphenyl]-2-[4-(Tetrahydropyran-2-yl)Oxy]Phenyl]Ethanone)

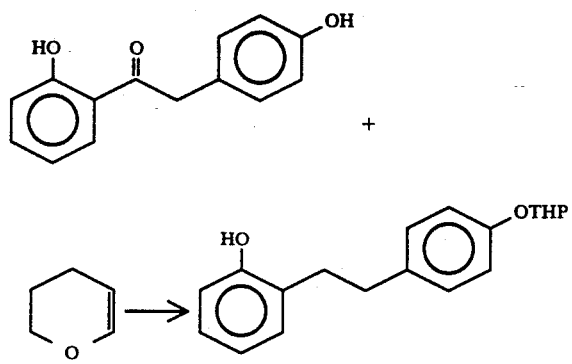

To a stirred solution of the deoxybenzoin (18.3 gm, 0.08 mole) and PTSA (100 mg) in dry dioxan (200 ml) was added dropwise a solution of 3,4-dihydro-2H-pyran (14.5 ml, 0.16 mole) in dry dioxan (100 ml) and the stirring was continued for 4 hours. The reaction mixture was then neutralised with methanolic ammonia (5 ml) and concentrated in vacuo. The residue was dissolved in ether (200 ml) and washed twice with 5% sodium hydroxide solution followed by water. The organic layer was dried ($Na_2SO_4$) and concentrated. The residue was chromatographed over a short silica gel column eluting rapidly with ethyl acetate-hexane (1:20, v/v)) to afford the title compound (20 gm, 80.1%) which was crystallised from hexane to m.p. 95° C.

EXAMPLE-AII

Preparation of
1-[2-Hydroxyphenyl]-2-[4-(Tetrahydropyran-2-yl)]Oxy]Phenyl]-3-[4-Hydroxyphenyl]Prop-2-Enone

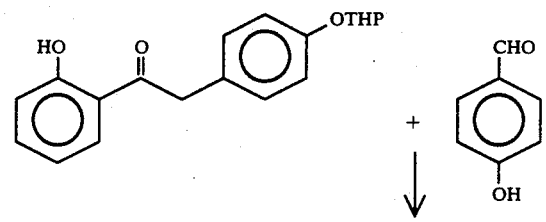

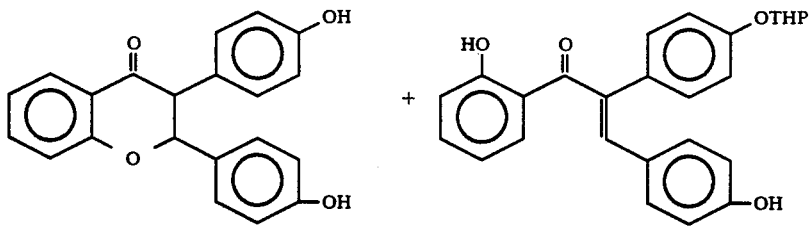

To a solution the monotetrahydropyranyl ether of the dihydroxydeoxybenzoin (6.87 g, 22 mmole) and 4-hydroxybenzaldehyde (2.44 gm, 20 mmole) in dry benzene (100 ml) was added dry piperidine (0.12 ml). It was refluxed for 30 hours removing water azeotropically adding fresh portions of dry benzene from time to time to replenish the distilled benzene. The reaction mixture was cooled and washed with water (2×40 ml). The organic layer was dried (Na$_2$SO$_4$) and concentrated. The residue left was allowed to stand for 24 hours. The solidified material was filtered off and washed with chloroform to afford the dihydrobenzopyranone. The filtrate was collected, concentrated and residue chromatographed over a silica gel column eluting rapidly with 2% ethyl acetate in hexane, to afford, first, the unreacted THP ether of deoxybenzoin (starting compound). With increasing polarity (20% ethyl acetate in hexane), the 2-phenylchalcone (desired compound) was obtained which was crystallised from benzene-hexane, m.p. 140° C. (6 g, 72.1%).

EXAMPLE - AIII

Preparation of 2[4-Hydroxyphenyl]-3-[4-[(Tetrahydropyran-2-yl]Oxy]Phenyl]-2H-1-Benzopyran

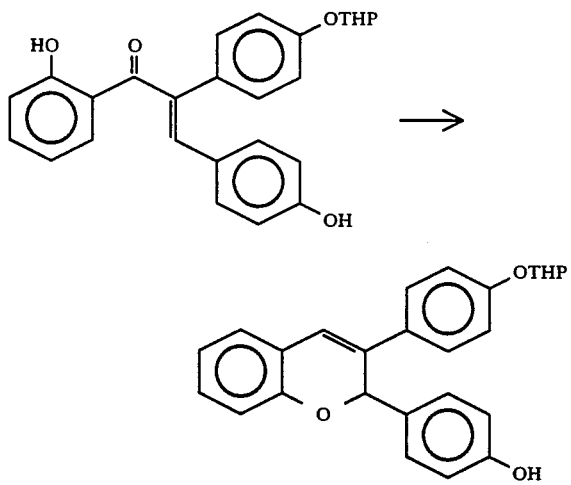

To a stirred solution of 2-phenylchalcone, prepared in example-AII, (4.16 gm, 10 mmole) in ethanol (50 ml) was added sodium borohydride (400 mg) in portions at an interval of 10–15 minutes and the stirring was continued for 15 hours. The ethanol was evaporated under vacuum and the residue was decomposed by adding saturated ammonium chloride solution until the pH was 8.0. The mixture was extracted with ethyl acetate. The organic layer was washed twice with water, dried and concentrated (Na$_2$SO$_4$). The residue was chromatographed over a silica gel column eluting with 10% ethyl acetate in hexane to afford the desired compound (2.4 gm, 60%) which was crystallised from benzene-hexane, m.p. 110° C.

EXAMPLE-AIV

2-[4-[2-(1-Piperidino)Ethoxy]Phenyl]-3-[4-Hydroxyphenyl]-2H-1-Benzopyrans

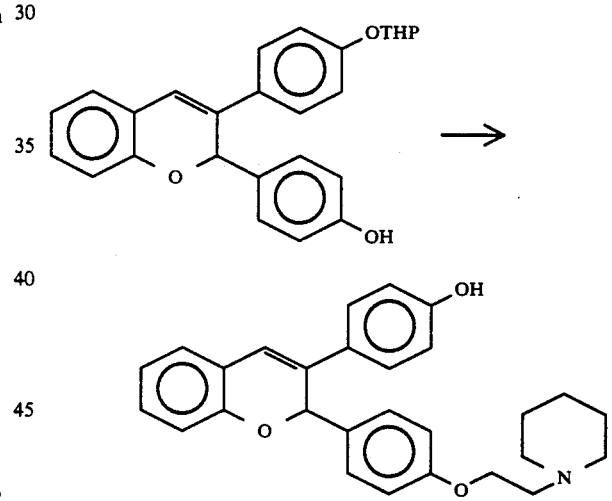

A mixture of the phenol prepared above in example AIII (800 mg, 2 mmole), 1-[2-chloroethyl) piperidine hydrochloride (590 mg, 3.2 mmole), anhydrous potassium carbonate (440 mg, 3.2 mmole) and dry acetone (20 ml) was stirred and refluxed for 35 hours. It was cooled and solid material filtered off and washed with acetone. The combined filtrate was concentrated and the residue chromatographed over a basic alumina column eluting with 2% ethyl acetate in hexane to afford the THP ether derivative (800 mg).

To a solution of this compound (800 mg) in ethanol (20 ml) was added 1 N hydrochloric acid (5 ml) and the solution was allowed to stand for 20 minutes. The ethanol was evaporated in vacuo, the residue treated with sodium bicarbonate solution (25 ml) and extracted twice with ethyl acetate. The organic layer was washed with water, dried (Na$_2$SO$_4$) and concentrated to afford the title compound of this invention (600 mg, 70.2%). It was crystallised from chloroformhexane, m.p. 110° C.

EXAMPLE-BI

Preparation of 1-[2-Hydroxy-4-Methoxyphenyl]-2-Phenyl-3-[4-Hydroxyphenyl]Prop-2-Enone

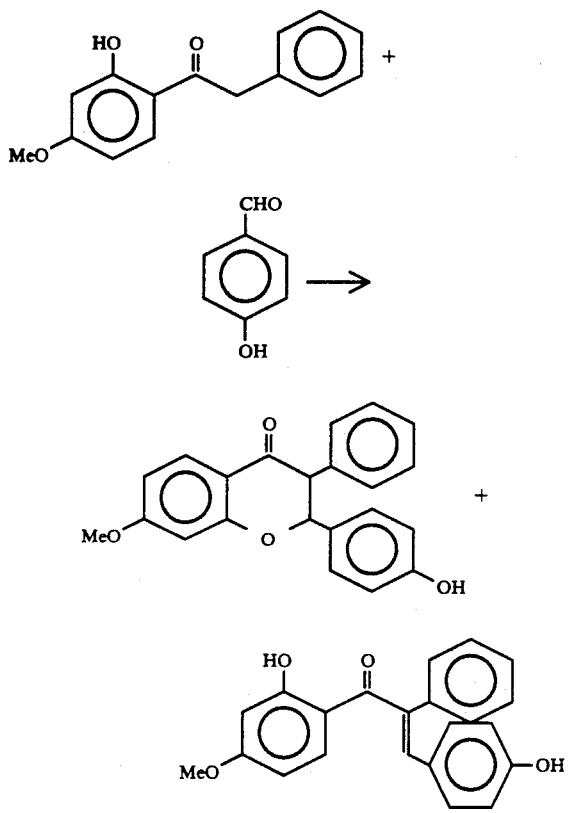

To a solution of deoxybenzoin i.e. 1-[2-hydroxy-4-methoxy-phenyl]-2-phenyl ethanone (12.1 g, 0.05 mole) and 4-hydroxy-benzaldehyde (6.1 g, 0.05 mole) in dry benzene (200 ml) was added dry piperidine (0.3 ml). The solution was refluxed for 30 hours removing water azeotropically and adding fresh proportions of dry benzene from lime to time to replenish its loss during the reaction. It was then cooled and washed twice with water. The organic layer was dried (Na2SO4) and concentrated. The residue was allowed to stand for 24 hour, the solidified material filtered and washed with chloroform to afford the dihydrobenzopyranone (4.0 g, 23.2%). It was crystallised from ethyl acetate-hexane, m.p. 195° C.

The combined filtrate left after the removal of dihydrobenzopyranone was concentrated and the residue subjected to chromatography over a silica gel column eluting with ethyl acetate - hexane to afford, first, the unreacted deoxybenzoin (staring material). Then, on increasing the solvent polarity, the 2-phenyl chalcone i.e. compound desired in this example was obtained (11.0 g, 65.3%). It crystallised from benzene-hexane, m.p. 150° C.

EXAMPLE-BII

Preparation of 2-[4-Hydroxyphenyl]-3-Phenyl-7-Methoxy-2H-1-Benzopyran

To a stirred solution of 2-phenylchalcone (prepared above in example-BI) (3.46 g, 10 mmole) in ethanol (15 ml) was added sodium borohydride (0.4 g) in three portions at 15 minute intervals and the stirring was continued for 12 hours. Ethanol was evaporated in vacuo and to the residue was added saturated ammonium chloride solution dropwise until the pH was 8.0. The mixture was extracted twice with ethyl acetate, the organic layer washed with water, dried (Na2SO4) and concentrated. The residue was chromatographed over a silica gel column eluting with ethyl acetate-hexane to afford the phenol desired under this example (2.5 g, 80%). It was crystallised from chloroform-hexane, m.p. 162° C.

EXAMPLE-BIII

Preparation of 2-[4-[2-(1-Pyrrolidino)Ethoxy]Phenyl]-3-Phenyl-7-Methoxy-2H-1-Benzopyran

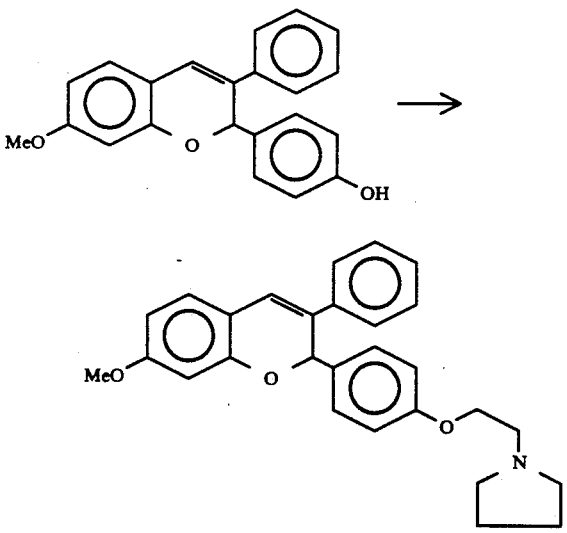

A mixture of the phenol prepared above in example-BII (660 mg, 2 mmole), 1-[2-chloro-ethyl) pyrrolidine hydrochloride (544 mg, 3.2 mmole), anhydrous potassium carbonate (440 mg, 3.2 mmole) and dry acetone (20 ml) was stirred and refluxed for 30 hours. On completion of the reaction (TLC), the reaction mixture was cooled, the solid material filtered off and washed with acetone. The combined filtrate was concentrated. The residue was chromatographed over a basic alumina column eluting with ethyl acetate - hexane to afford the pyrrolidino ether desired in this example (671 mg, 78.6%). It was crystallised from hexane, m.p. 99° C.

EXAMPLE-BIV

Preparation of 2-[4-[2-(1-Piperidino)Ethoxy]Phenyl]-3-Phenyl-7-Methoxy-2H-1-Benzopyran

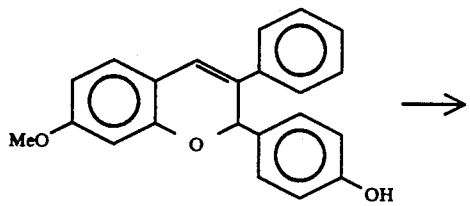

A mixture of phenol prepared above in example-BII (660 mg, 2 mmole), 1-[2-chloroethyl] piperidine hydrochloride (590 mg, 3.2 mmole), anhydrous potassium carbonate (440 mg, 3.2 mmole) and dry acetone (20 ml) was stirred and refluxed for 30 hours. On completion of the reaction (TLC), it was cooled, the solid material filtered off and washed with acetone. The combined filtrate was concentrated. The residue was chromatographed over a column of basic alumina eluting with ethyl acetate - hexane to afford the compound desired in this specification (717 mg, 81.5%).

EXAMPLE-CI

Preparation of 1-[2-Hydroxy-4-[Tetrahydropyran-2-yl)Oxy]Phenyl]-2-[4-[(Tetrahydropyran-2-yl) Oxy]Phenyl]Ethanone

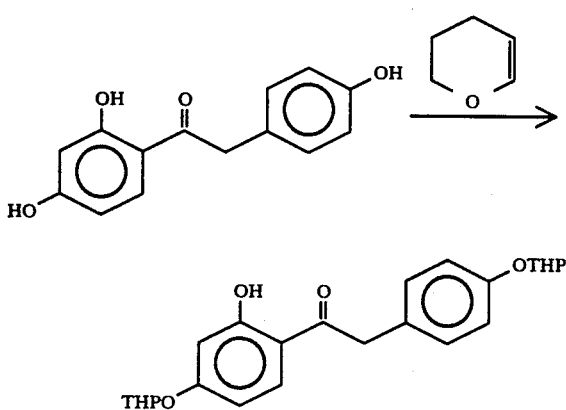

To the starting deoxybenzoin (2.44 g, 10 mmole) shown above, cooled in an ice bath, was added a mixture of 3,4-dihydro-2H-pyran (10 ml, 110 mmole) and concentrated hydrochloric acid (0.01 ml). The reaction mixture was stirred for 4 hours. It was then diluted with ether (100 ml) and washed thrice with 5% sodium hydroxide solution followed by water. The ethereal layer was dried ($Na_2SO_4$) and concentrated. The oily residue was crystallised from hexane to afford (3.87 g, 94% yield of the title compound, m.p. 118° C.

EXAMPLE-CII

Preparation of 2-[4-Hydroxyphenyl]-3-[4-[(Tetrahydropyran-2-yl)Oxy]Phenyl]-7-[4-(Tetrahydropyran-2-yl)Oxy]-2,3-Dihydro-4H-1-Benzopyran-4-One and 1-[2-Hydroxy-4-[(Tetrahydropyran-2-yl)Oxy]Phenyl]-2-[4-[(Tetrahydropyran-2-yl)Oxy]Phenyl]-3-[4-Hydroxyphenyl]Prop-2-Enone

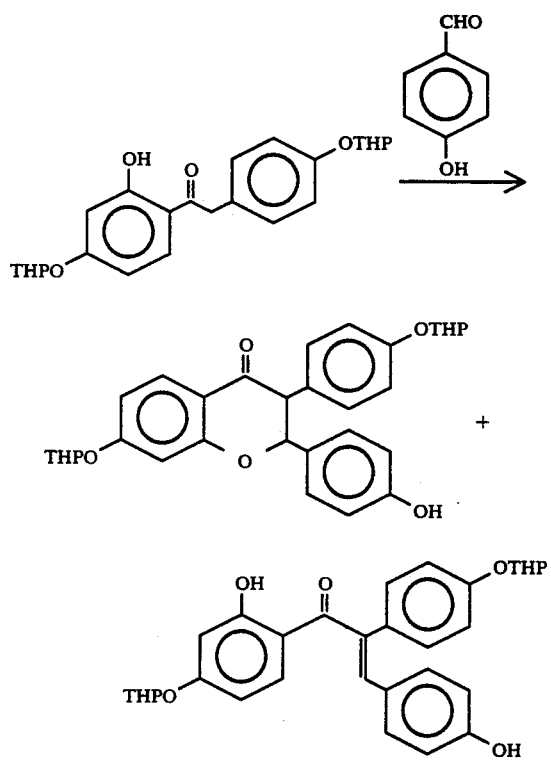

To a solution of bis (tetrahydropyranyl) ether of deoxybenzoin (4.12 g, 10 mmol), prepared above and 4-hydroxybenzaldehyde (1.22 g, 10 mmole) in dry benzene (100 ml) was added dry piperidine (0.01 ml). The reaction mixture was refluxed for 30 hours removing water azeotropically and adding dry benzene from time to time, if needed, to replenish loss during the reaction. The reaction mixture was cooled and washed twice with water. The organic layer was dried ($Na_2SO_4$) and concentrated. The residue was chromatographed over a silica gel column eluting with ethyl acetatehexane mixture to afford the unreacted deoxybenzoin ether. Then on increasing the solvent polarity a mixture of the dihydrobenzopyranone and 2-phenylchalcone was obtained. The dihydrobenzopyranone (1.2 g, 23%), m.p. 190° C., was separated by crystallisation from a mixture of ethyl acetate-hexane leaving behind the 2-phenylchalcone as an oily residue in the mother liquor. The 2-phenylchalcone (2.3 g, 44%) was used in the next step without purification.

EXAMPLE-CIII

Preparation of
2-[Hydroxyphenyl]-3-[4-[(Tetrahydropyran-2-yl)Oxy]-Phenyl]-7-[(Tetrahydropyran-2-yl)Oxy]

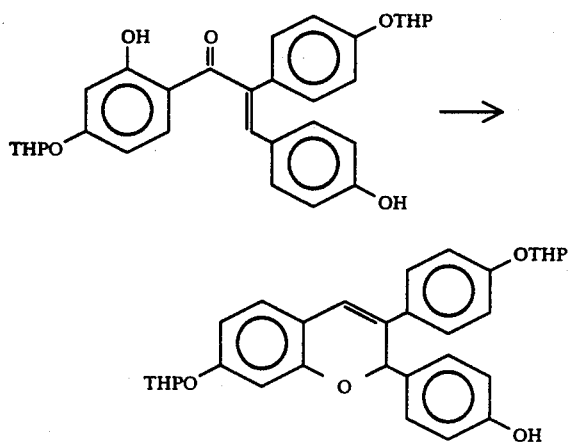

To a stirred solution of the 2-phenylchalcone (1.29 g, 2.5 mmole), prepared above in example-CII in ethyl alcohol (20 ml) was added sodium borohydride (100 mg) in different portions at an interval of 10-15 minutes at room temperature and the stirring was continued for 12 hours. Ethyl alcohol was evaporated in vacuo, and to the residue was added saturated ammonium chloride solution dropwise until the pH was 8.0. The mixture was extracted twice with ethyl acetate, the organic layer washed with water, dried ($Na_2SO_4$) and concentrated. The residue was purified by flash chromatography over a silica gel column eluting with ethyl acetate-hexane to afford the title phenol (940 mg, 75%), which was crystallised from chloroform-hexane, m.p. 180° C.

EXAMPLE-CIV

Preparation of
2-[4-[2-(1-Piperidino)Ethoxy]Phenyl]-3-[4-Hydroxyphenyl]-7-Hydroxy-2H-1-Benzopyran

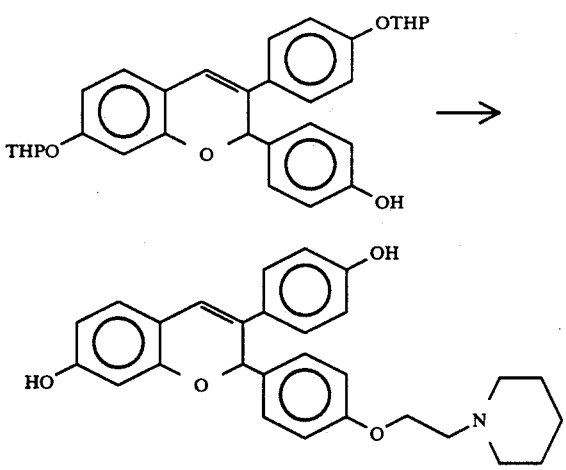

A mixture of the phenol (1.0 g, 2 mmole), prepared above in example-CIII, and 1-[2-chloroethyl] piperidine hydrochloride (590 mg, 3.2 mmole), anhydrous potassium carbonate (440 mg, 3.2 mmole) and dry acetone 30 ml was stirred and refluxed for 30 hours. On completion of the reaction (TLC), it was cooled, the solid material filtered and washed with acetone. The combined filtrate was concentrated and the residue chromatographed over a basic alumina column eluting with ethyl acetate-hexane to afford (1.1 g) of an oil residue. This was dissolved in ethyl alcohol (20 ml) and to it was added 1N hydrochloric acid (10 ml) and the solution was allowed to stand for 20 minutes. It was then concentrated in vacuo, the residue treated with saturated sodium bicarbonate solution (20 ml) and extracted with ethyl acetate.

The organic layer was washed with water, dried ($Na_2SO_4$) and concentrated to afford (625 mg, 70%) an oily residue i.e. the compound desired in this example which was crystallised as its oxalate from ethyl alcohol-dry ether, m.p. 190° C. The above compound on desired alkylation or acylation at one or both of the hydroxy groups affords other products of compound I.

The present invention provides compounds of the formula I as described above for use in a method of medical treatment.

The invention also provides for the use of compounds of the formula I in the manufacture of a medicament for use in a method of treatment of an estrogen-dependent condition such as breast cancer.

The compounds may be administered in the form of a pharmaceutical composition. The present invention provides a composition comprising a compound of formula I and a pharmaceutically acceptable carrier or diluent.

The compositions may be administered orally or parenterally, in a dosage of 1 to 1000 μg per kilogram of body weight of a subject to be treated, depending on factors such as the particular condition to be treated and the route of administration.

We claim:

1. A compound of the formula I

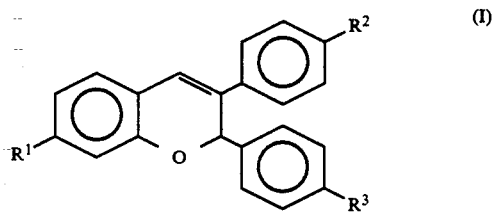

wherein $R^1$ and $R^2$, which may be the same or different, are each —H, —OH, alkoxy of 1 to 17 carbon atoms or alkoxycarbonyl of 2 to 18 carbon atoms, and $R^3$ is

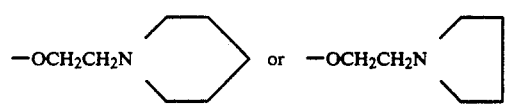

2. A compound as claimed in claim 1 in which $R^1$ and $R^2$ are each independently H, OH or $C_{1-4}$alkoxy.
3. A compound as claimed in claim 1 in which $R^1$ is H.
4. A compound as claimed in claim 1 in which $R^3$ is

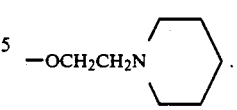

5. 2-[4-[2-(1-piperidino)ethoxy]phenyl]-3-[4-hydroxyphenyl]-2H-1-benzopyran according to claim 1.

6. 2-[4-[2-(1-piperidino)ethoxy]phenyl]-3-phenyl-7-methoxy-2H-1-benzopyran according to claim 1.

7. 2-[4-[2-(1-piperidino)ethoxy]phenyl]-3-[4-hydroxyphenyl]-7-hydroxy-2H-1-benzopyran according to claim 1.

8. A composition which comprises an antiestrogenic effective amount of a compound according to claim 1 and a pharmaceutically acceptable carrier or diluent.

9. A method for inhibiting the action of estrogen in a mammal comprising administering to said mammal a compound according to claim 1 in an amount effective to inhibit the action of the estrogen in said mammal.

10. A method according to claim 9 in which the compound is administered orally at a dosage of from 1 to 1000 µg per kilogram of body weight of said mammal.

11. A method according to claim 9, in which the subject has an estrogen dependent condition.

12. A method according to claim 11, in which the compound is administered parenterally at a dosage of 1 to 1000 µg per kilogram of body weight of the subject.

* * * * *